US008702589B2

(12) United States Patent
Kuyava

(10) Patent No.: US 8,702,589 B2
(45) Date of Patent: Apr. 22, 2014

(54) SYSTEM TO TRANSPORT COMPONENTS OF IMPLANTABLE PENILE PROSTHESES

(75) Inventor: Charles C. Kuyava, Eden Prairie, MN (US)

(73) Assignee: AMS Research Corporation, Minnetonak, MN (US)

(*) Notice: Subject to any disclaimer, the term of this patent is extended or adjusted under 35 U.S.C. 154(b) by 819 days.

(21) Appl. No.: 12/646,149

(22) Filed: Dec. 23, 2009

(65) Prior Publication Data
US 2010/0160723 A1 Jun. 24, 2010

Related U.S. Application Data

(60) Provisional application No. 61/140,382, filed on Dec. 23, 2008.

(51) Int. Cl.
A61F 5/00 (2006.01)

(52) U.S. Cl.
USPC .......................................... 600/40

(58) Field of Classification Search
USPC ................... 600/38–41; 206/438
See application file for complete search history.

(56) References Cited

U.S. PATENT DOCUMENTS

| 3,954,102 | A | | 5/1976 | Buuck |
|---|---|---|---|---|
| 3,987,789 | A | | 10/1976 | Timm et al. |
| 4,244,370 | A | | 1/1981 | Furlow et al. |
| 4,267,829 | A | | 5/1981 | Burton et al. |
| 4,300,442 | A | * | 11/1981 | Martin .................. 99/289 R |
| 4,383,525 | A | | 5/1983 | Scott et al. |
| 4,392,562 | A | | 7/1983 | Burton et al. |
| 4,407,278 | A | | 10/1983 | Burton et al. |
| 4,590,927 | A | | 5/1986 | Porter et al. |
| 4,594,998 | A | | 6/1986 | Porter et al. |
| 4,790,810 | A | | 12/1988 | Pugh, Jr. et al. |
| 4,807,608 | A | | 2/1989 | Levius |
| 4,875,472 | A | | 10/1989 | Levius |
| 4,895,139 | A | | 1/1990 | Hauschild et al. |
| 5,010,882 | A | | 4/1991 | Polyak et al. |
| 5,048,510 | A | | 9/1991 | Hauschild et al. |
| 5,171,272 | A | | 12/1992 | Levius |
| 5,263,981 | A | | 11/1993 | Polyak et al. |
| 5,512,033 | A | | 4/1996 | Westrum, Jr. et al. |
| 5,553,379 | A | | 9/1996 | Westrum, Jr. et al. |
| 5,704,895 | A | | 1/1998 | Scott et al. |
| 6,443,887 | B1 | | 9/2002 | Derus et al. |
| 2002/0082471 | A1 | | 6/2002 | Henkel et al. |
| 2002/0082472 | A1 | | 6/2002 | Derus et al. |
| 2002/0082709 | A1 | | 6/2002 | Almli et al. |
| 2002/0091302 | A1 | | 7/2002 | Kuyava et al. |

OTHER PUBLICATIONS

American Medical Systems, AMS Ambicor® Penile Prosthesis Operating Room Manual, 2003, pp. 1-8.
American Medical Systems, "AMS 700® Penile Prosthesis Operating Room Manual", 2004, pp. 1-27.

* cited by examiner

Primary Examiner — John Lacyk
(74) Attorney, Agent, or Firm — Kagan Binder, PLLC

(57) ABSTRACT

A delivery tool and related methods for transporting a pre-assembled implantable penile prosthesis to an operating room. The delivery tool includes at least a first cap with receptacles for receiving and retaining pre-connected components during transport to prevent shifting, tangling and/or damage to the pre-connected components. The receptacles can be adapted for receiving pre-connected components, tubing used to connect the components, as well as stand-alone components that are utilized during a surgical procedure. The delivery tool can include cushioning elements for protecting the pre-connected components from damage caused by shifting during transport.

17 Claims, 4 Drawing Sheets

SYSTEM TO TRANSPORT COMPONENTS OF IMPLANTABLE PENILE PROSTHESES

PRIORITY CLAIM

The present application claims priority to U.S. Provisional Application Ser. No. 61/140,382, filed Dec. 23, 2008, and entitled "SYSTEM TO MANAGE CYLINDERS AND PRE-LOADED NEEDLE HOLDER," which is herein incorporated by reference in its entirety.

FIELD OF THE INVENTION

The present invention is directed to an apparatus and related methods for transporting components of implantable penile prostheses. More specifically, the present invention is directed to a delivery tool for transporting a pre-assembled implantable penile prosthesis so as to avoid entanglement and damage to connected components during transport.

BACKGROUND OF THE INVENTION

Implantation of an implantable penile prosthesis (IPP) is a common treatment device for treating erectile dysfunction and other penile ailments. Typically, an implantable penile prosthesis comprises at least two inflatable cylinders connected to a pump by kink resistant tubing. In other versions, an implantable penile prosthesis can further comprise a reservoir for storing a liquid solution for inflating the inflatable cylinder and is connected to the pump or the inflatable cylinder by kink resistant tubing. Representative implantable penile prosthesis devices can include the AMBICOR or AMS 700, both available from American Medical Systems of Minnetonka, Minn.

Many of the components of the implantable penile prosthesis can be pre-assembled by the manufacturer rather than having operating room personnel fully assemble the prosthesis prior to or during the procedure. For example, the manufacturer can pre-connect the inflatable cylinder to the pump or reservoir by kink resistant tubing such that minimal assembly is required in the operating room before the prosthesis is implanted. Other components are pre-connected by the manufacturer for specific surgical purposes and are later disconnected by operating room personnel when the purpose is met. For example, each inflatable cylinder can be pre-connected to a pre-loaded syringe containing an inflating solution for loading the inflatable cylinder during the operation. During the operation, the inflating solution is transferred from the syringe into the inflatable cylinder, after which the pre-loaded syringe is disconnected from the inflatable cylinder and discarded. Pre-connecting the syringe to the inflatable cylinder insures that the proper amount of inflating solution is transferred to the inflatable cylinder. Pre-assembling components reduces operating time and decreases the likelihood that the procedure will be performed incorrectly or that the prosthesis will be incorrectly assembled.

Although pre-assembling components decreases the operating time and reduces the likelihood of surgical error, pre-connecting the various components can result in the components becoming tangled during transport. Typically, all the components of an implantable penile prosthesis are packaged and transported together in a single sterile package. Generally, the components are loosely packed into the sterile package which can result in the components becoming tangled as the components shift during transport. If the pre-assembled components are tangled during transport, operating room personnel must untangle the components before continuing the procedure, substantially increasing the time necessary to complete the procedure and causing frustration for operating room personnel.

An additional consideration is that the components of an implantable penile prosthesis are generally discrete and lightweight due to their implantable nature. As such, the components can be easily damaged. The pre-assembled components often comprise fragile materials such as, for example, elastomers that are particularly susceptible to damage. The tangling and subsequent untangling of the components can result in damage to the components and compromise the effectiveness of the implantable penile prosthesis. Similarly, as the components are typically placed in the sterile package unrestrained, the components can jostle together further damaging the components.

As such, there exists a need for improvements in the manner in which connected components of a pre-assembled implantable penile prosthesis are prevented from becoming entangled or otherwise damaged during transport.

SUMMARY OF THE INVENTION

A representative embodiment of the current disclosure is directed to a delivery tool for transporting connected components for a pre-assembled implantable penile prosthesis. More specifically, the delivery tool comprises receptacles for receiving the components of the pre-assembled implantable penile prosthesis and retaining the components during transport to prevent tangling of the pre-connected components or jostling of the components. The receptacles can be adapted for receiving in the individual components, tubing used to connect the components, and unconnected components that are subsequently connected as part of the surgical procedure. The delivery tool can further comprise cushioning elements so at to protect the components from damage caused by shifting during transport.

In another representative embodiment, a delivery tool can comprise a cap having a cushioning element disposed within the cap. The cushioning element can define a plurality of receptacles for receiving components and holding the components until manually removed by operating room personnel. The component can be inserted into one of the receptacles such that the receptacle grips the component end and secures the cap to the component. The cushioning element can further comprise notches connecting multiple receptacles. Pre-connected components linked by tubing can be inserted into receptacles linked by notches such that each pre-connected component is individually held by a receptacle and the tubing linking the pre-connected components is disposed within the notch.

Another representative embodiment of the delivery tool can comprise a first and a second cap each having a cushioning element defining a plurality of receptacles. The receptacles defined by the first cap are adapted to receive the first ends of components, while second receptacles defined by the second cap are adapted to receive the opposed second ends of components. The first and second caps can simultaneously grip both ends of the components providing added structure to the delivery tool, thereby preventing the components from shifting and contacting the other components as well as generally protecting both ends of the components from damage during transport. The first and second caps can be adapted to receive both ends of all components to be transported. Alternatively, in a single delivery tool, some of the components are gripped at both ends by the first and second caps, while other components are gripped by only the first or second cap respectively.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

Figure 1:
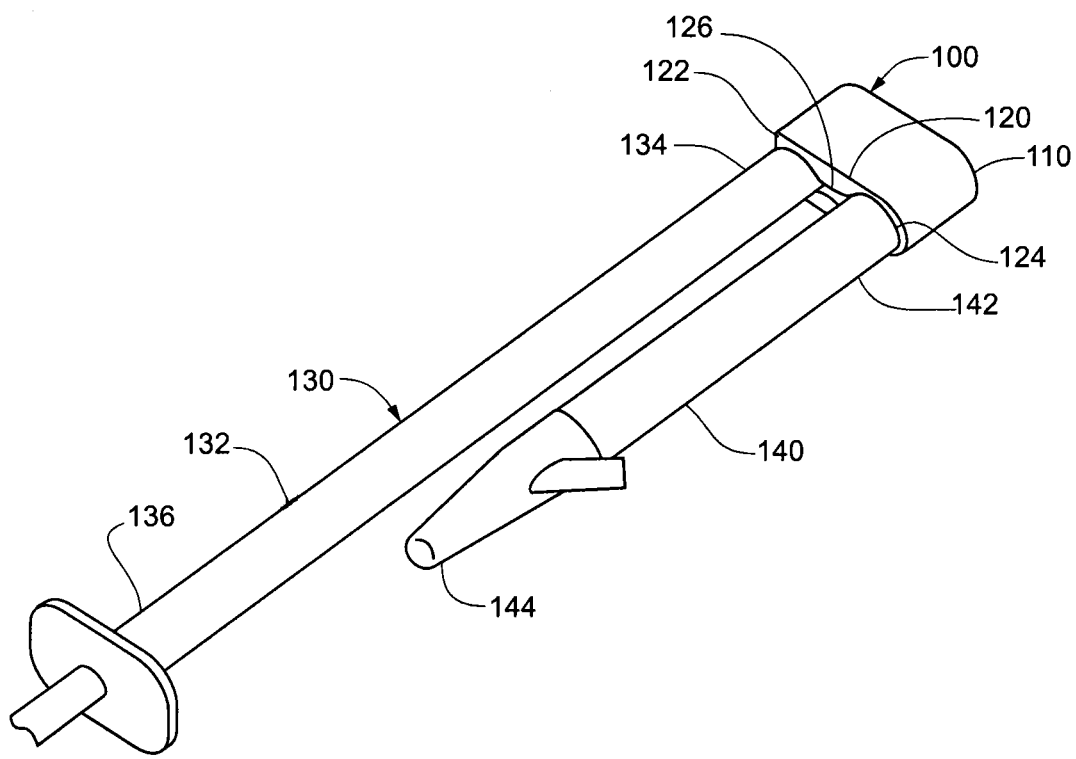
FIG. 1 is a perspective view of a representative embodiment of a delivery tool for securing a pre-assembled implantable penile prosthesis according to the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

As illustrated in FIG. 1, a pre-assembled implantable penile prosthesis 130 can comprise a first pre-connected component 132 such as, for example, a needle delivery tool linked to a second pre-connected component 140, such as, for example, a cylinder. First pre-connected component 132 generally defines a first end 134 and a second end 136 while second pre-connected component 140 defines a first end 142 and a second end 144. The first pre-connected component 132 is connected to the second pre-connected component 140 by tubing (not depicted) extending from first end 134 of the first pre-connected component 132 to the first end 142 of the second pre-connected component 140.

As depicted in FIG. 1, delivery tool 100 comprises a cap 110 having a cushioning element 120 disposed within the cap 110. The cushioning element 120 defines a first receptacle 122 and a second receptacle 124. Cap 110 is fitted over the pre-assembled implantable penile prosthesis 130 by inserting first end 134 of the first pre-connected component 132 into the first receptacle 122 and the first end 142 of the second pre-connected component 140 into the second receptacle 124. As illustrated, first and second receptacles 122, 124 can have different diameters to accommodate the different sizes of the first and second pre-connected components 132, 140. First and second receptacles 122, 124 can be similarly or differently sized according to the type of component to be gripped. Alternatively, the cushioning element 120 can further comprise a notch 126 connecting the first receptacle 122 to the second receptacle 124. Tubing linking the first and second pre-connected components 132, 140 is insertable into the notch 126 such that the tubing is also gripped and retained by the cap 110.

In one embodiment, cap 110 can comprise a molded silicone elastomer having sufficient rigidity to secure the components. Alternatively, cap 110 can comprise other sufficiently rigid or semi-rigid materials providing sufficient support to secure the components. Cushioning element 120 can comprise elastic foam, rubber or other elastic material that reduces impact sustained at cap 110 and stretches when either first or second pre-connected component 132, 140 is inserted into the corresponding receptacle 122, 124 to provide a gripping pressure for retaining the first or second pre-connected component 132, 140 within the cap 110. Cushioning element 120 can also comprise a high friction material such as, for example, an resilient foam, rubber or similar material that can statically grip the first or second pre-connected component 132, 140 without stretching, while also protecting first or second pre-connected component 132, 140.

Figure 2:
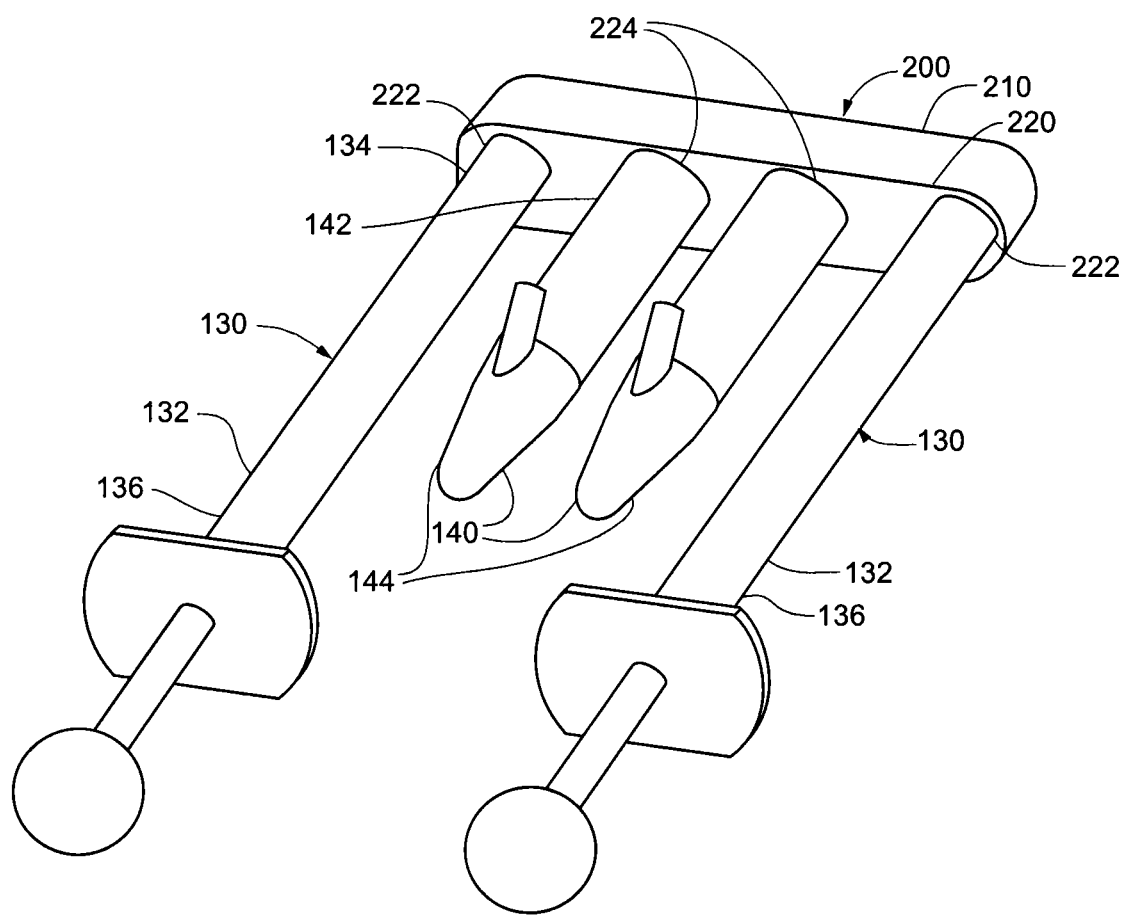
FIG. 2 is a perspective view of a representative embodiment of a delivery tool for securing a pre-assembled implantable penile prosthesis according to the present disclosure.

As illustrated in FIG. 2, another representative embodiment of delivery tool 200 can comprise an elongated cap 210 having a cushioning element 220 defining paired sets of first and second receptacles 222, 224 for securing pre-assembled implantable penile prosthesis 130. Elongated cap 210 can be extended such that the cushioning element 220 can define sufficient receptacles 222,224 for any configuration/size of pre-assembled implantable penile prosthesis 130.

Figure 3:
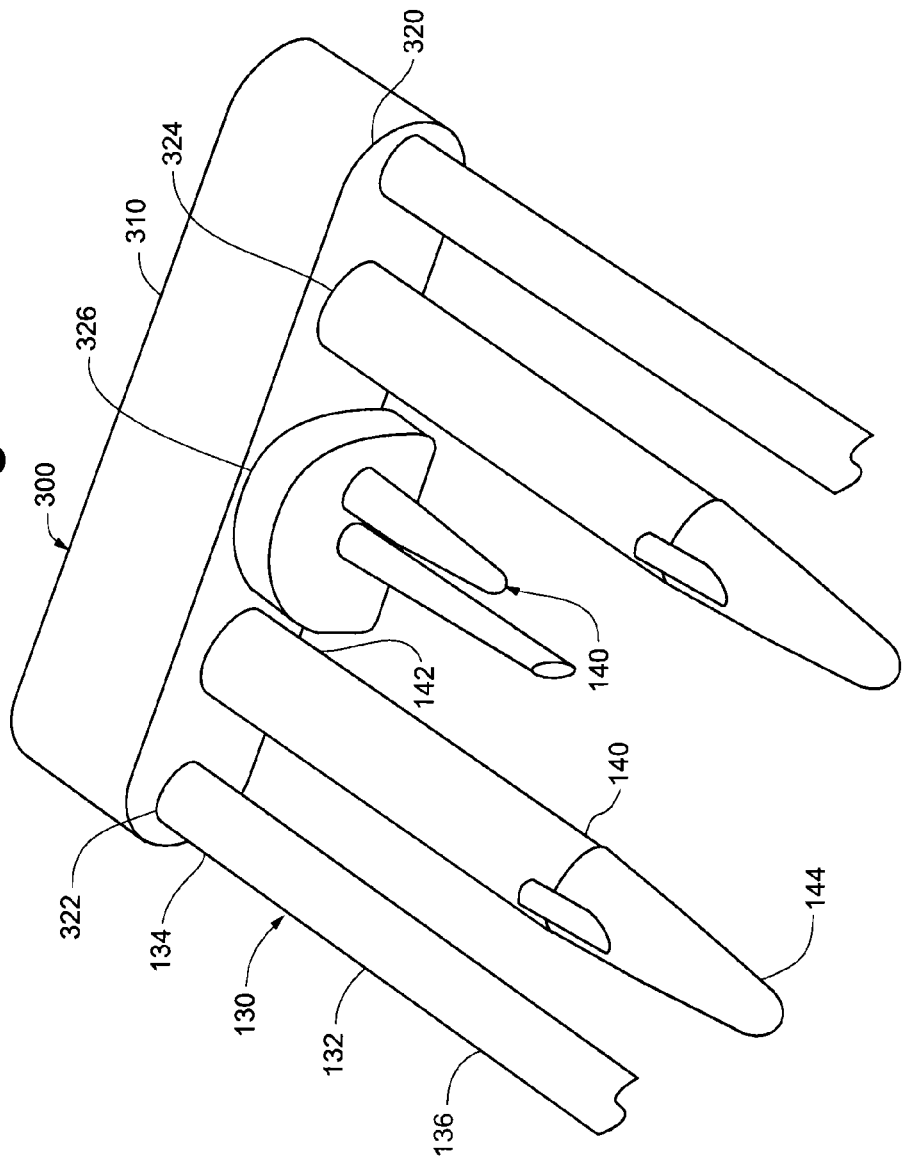
FIG. 3 is a perspective view of a representative embodiment of a delivery tool for securing a pre-assembled implantable penile prosthesis and an unconnected component according to the present disclosure.

Referring to FIG. 3, an embodiment of a delivery tool 300 can be configured for transporting both a pre-assembled implantable penile prosthesis 130 and a stand-alone component 140. Delivery tool 300 can comprise an elongated cap 310 having a cushioning element 320 defining a plurality of first and second receptacles 322, 324. Cushioning element 320 further defines a third receptacle 326 for receiving a securable end 146 of the stand-alone component 140. The elongated cap 310 can be extended such that the cushioning element 320 can define sufficient receptacles 322, 324, 326 for any number of pre-connected component 132, 140 and unconnected components 140.

Figure 4:
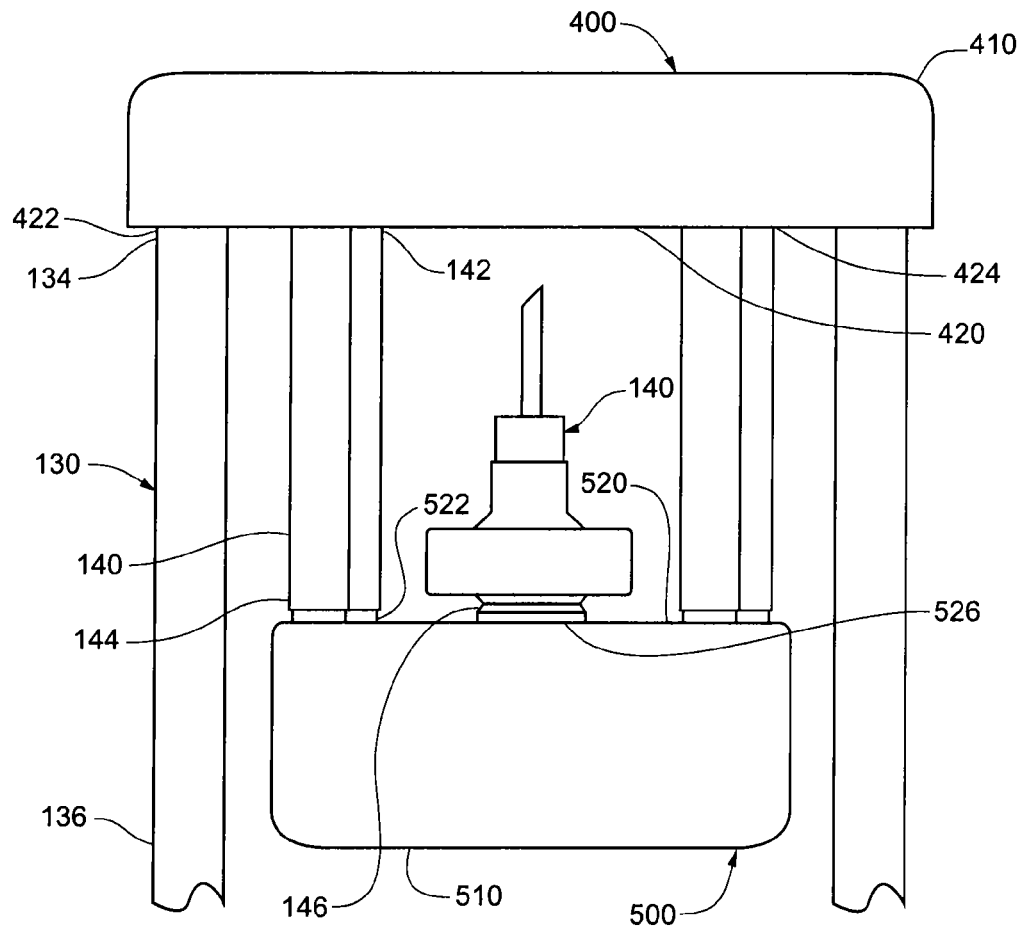
FIG. 4 is a perspective view of a representative embodiment of a delivery tool for securing a pre-assembled implantable penile prosthesis and an unconnected component according to the present disclosure.

As depicted in FIG. 4, another representative embodiment of a delivery tool 400 can comprise a first cap 410 and a second cap 520. First cap 410 comprises a first cushioning element 420 defining a plurality of receptacles 422 for receiving first ends 134, 142 of a pre-assembled implantable penile prosthesis 130. Second cap 510 comprises a second cushioning element 520 defining a plurality of receptacles 522 for receiving the second ends 136, 144 of a pre-assembled implantable penile prosthesis 130. The second cushioning element 520 can further define a third receptacle 526 for receiving a securable end 146 of the stand-alone component 140.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative embodiments.

The invention claimed is:

1. A delivery tool for securing components of a pre-assembled implantable penile prosthesis that comprises a first component having first and second ends and a second component having first and second ends, the delivery tool comprising:

a first cap including a first cushioning element disposed within the first cap, the cushioning element defining at least a first receptacle and a second receptacle, each receptacle adapted to removably receive one of the first end of the first component and the first end of the second component, and a second cap including a second cushioning element, the second cushioning element defining at least a first receptacle adapted to removably receive the second end of one of the first component and the second component, wherein the first cap retains the first ends of the first and second components and the second cap retains the second end of one of the first and second components to prevent shifting of the first and second components during transport.

2. The delivery tool of claim 1, wherein the first and second components are operably connected by tubing and wherein the cushioning element includes a notch for retaining the tubing.

3. The delivery tool of claim 1, wherein the cushioning element further comprises a third receptacle, and wherein the third receptacle is adapted to receive a stand-alone component and wherein the third receptacle retains the stand-alone component to prevent shifting of the stand-alone component during transport.

4. The delivery tool of claim 1, wherein one of the first cap or the second cap includes a third receptacle adapted to receive a stand-alone component.

5. A shipping assembly for delivery to an operating room, comprising:
a pre-assembled implantable penile prosthesis including at least first and second components, the first and second components being operably connected and the first and second components each having a first end and a second end; and
a delivery tool for securing components of the pre-assembled implantable penile prosthesis, the delivery tool including a first cap having at least two receptacles adapted to receive the first ends of the first and second components and a second cap defining at least a first receptacle adapted to removably receive a corresponding second end of one of the first component and the second component, wherein the first and second receptacles of the first cap retain corresponding first ends of the first and second components and the at least one receptacle of the second cap retains the corresponding second end of one of the first and second components such that the first and second caps cooperatively prevent shifting of the first and second components during transport.

6. The shipping assembly of claim 5, wherein the first and second components are operably connected with a length of tubing.

7. The shipping assembly of claim 6, wherein the first cap includes a notch, and wherein the length of tubing is retained within the notch during transport.

8. The shipping assembly of claim 5, wherein the pre-assembled implantable penile prosthesis further comprises a stand-alone component, and wherein the first cap further comprises a third receptacle, and wherein the third receptacle is adapted to receive the stand-alone component to prevent shifting of the third component during transport.

9. The shipping assembly of claim 8, wherein the first component comprises a needle delivery tool, the second component comprises a cylinder and the stand-alone component comprises a pump.

10. The shipping assembly of claim 5, wherein the pre-assembled implantable penile prosthesis further comprises a stand-alone component, and wherein one of the first and second caps further comprises a third receptacle, and wherein the third receptacle is adapted to receive the stand-alone component to prevent shifting of the third component during transport.

11. The shipping assembly of claim 10, wherein the first component comprises a needle delivery tool, the second component comprises a cylinder and the stand-alone component comprises a pump.

12. A method for supplying a pre-assembled implantable penile prosthesis to an operating room, comprising:
providing a pre-assembled implantable penile prosthesis having a first component operably connected to a second component, both the first and second component having a first end;
providing a first cap defining at least a first pair of receptacles;
inserting the first ends of the first and second components into the receptacles;
providing a second cap defining at least one receptacle;
inserting a corresponding second end of one of the first and second components into the corresponding receptacle of the second cap; and
retaining positions of the first and second components using the first and second caps during transport to an operating room.

13. The method of claim 12, wherein the first and second components are operably connected with a length of tubing and wherein the method further comprises:
positioning the length of tubing within a notch in the first cap.

14. The method of claim 12, wherein the implantable penile prosthesis further comprises a stand-alone component, and wherein the first cap further comprises a third receptacle, and wherein the method further comprises:
inserting the stand-alone component into the third receptacle; and
retaining the position of stand-alone component during transport to the operating room.

15. The method of claim 12, wherein the implantable penile prosthesis further comprises a stand-alone component, and wherein one of the first cap and second cap further comprises a third receptacle, and wherein the method further comprises:
inserting the stand-alone component into the third receptacle; and
retaining the position of the stand-alone component during transport to the operating room.

16. The delivery tool of claim 1, wherein the implantable penile prosthesis further comprises third and fourth components that each have a first end and a second end, wherein the first cushioning element further comprises third and fourth receptacles, each receptacle adapted to removably receive one of the first end of the third component and the first end of the fourth component, and wherein the second cushioning element further comprises at least a second receptacle adapted to removably receive the second end of one of the third component and the fourth component.

17. The shipping assembly of claim 5, wherein the implantable penile prosthesis further comprises third and fourth components that are operably connected and that each have a first end and a second end, wherein the first cap further comprises at least four receptacles for receiving the first ends of the first, second, third, and fourth components, and wherein the second cap includes at least a second receptacle adapted to removably receive a second end of at least one of the third component and the fourth component.

\* \* \* \* \*

UNITED STATES PATENT AND TRADEMARK OFFICE
CERTIFICATE OF CORRECTION

PATENT NO. : 8,702,589 B2
APPLICATION NO. : 12/646149
DATED : April 22, 2014
INVENTOR(S) : Charles C. Kuyava Page 1 of 1

It is certified that error appears in the above-identified patent and that said Letters Patent is hereby corrected as shown below:

IN THE SPECIFICATION: In Column 4, Line 43, delete "520." and insert -- 510. --, therefor.

Signed and Sealed this
Fifth Day of January, 2016

Michelle K. Lee
*Director of the United States Patent and Trademark Office*